United States Patent [19]

Hewett et al.

[11] Patent Number: 5,013,353

[45] Date of Patent: May 7, 1991

[54] HERBICIDAL METHOD USING DIFLUFENICAN

[75] Inventors: Richard H. Hewett, Thaxted; Ponnan Veerasekaran, Ongar, both of England

[73] Assignee: May & Baker Limited, Dagenham, United Kingdom

[21] Appl. No.: 537,944

[22] Filed: Jun. 14, 1990

Related U.S. Application Data

[62] Division of Ser. No. 881,006, Jul. 1, 1986.

[30] Foreign Application Priority Data

Jul. 2, 1985 [GB] United Kingdom ................. 8516764
Oct. 30, 1985 [GB] United Kingdom ................. 8526733

[51] Int. Cl.$^5$ .................... A01N 43/40; A01N 47/28; B65D 79/00

[52] U.S. Cl. .......................................... 71/94; 71/119; 426/106

[58] Field of Search ...................... 71/94, 119; 426/106

[56] References Cited

FOREIGN PATENT DOCUMENTS 2087887 6/1982 United Kingdom .

Primary Examiner—Richard L. Raymond
Assistant Examiner—B. Bembenick
Attorney, Agent, or Firm—Burns, Doane, Swecker & Mathis

[57] ABSTRACT

The invention provides a method of controlling the growth of weeds using (a) a urea herbicide and (b) diflufenican; herbicidal compositions comprising (a) and (b) are described.

4 Claims, 5 Drawing Sheets

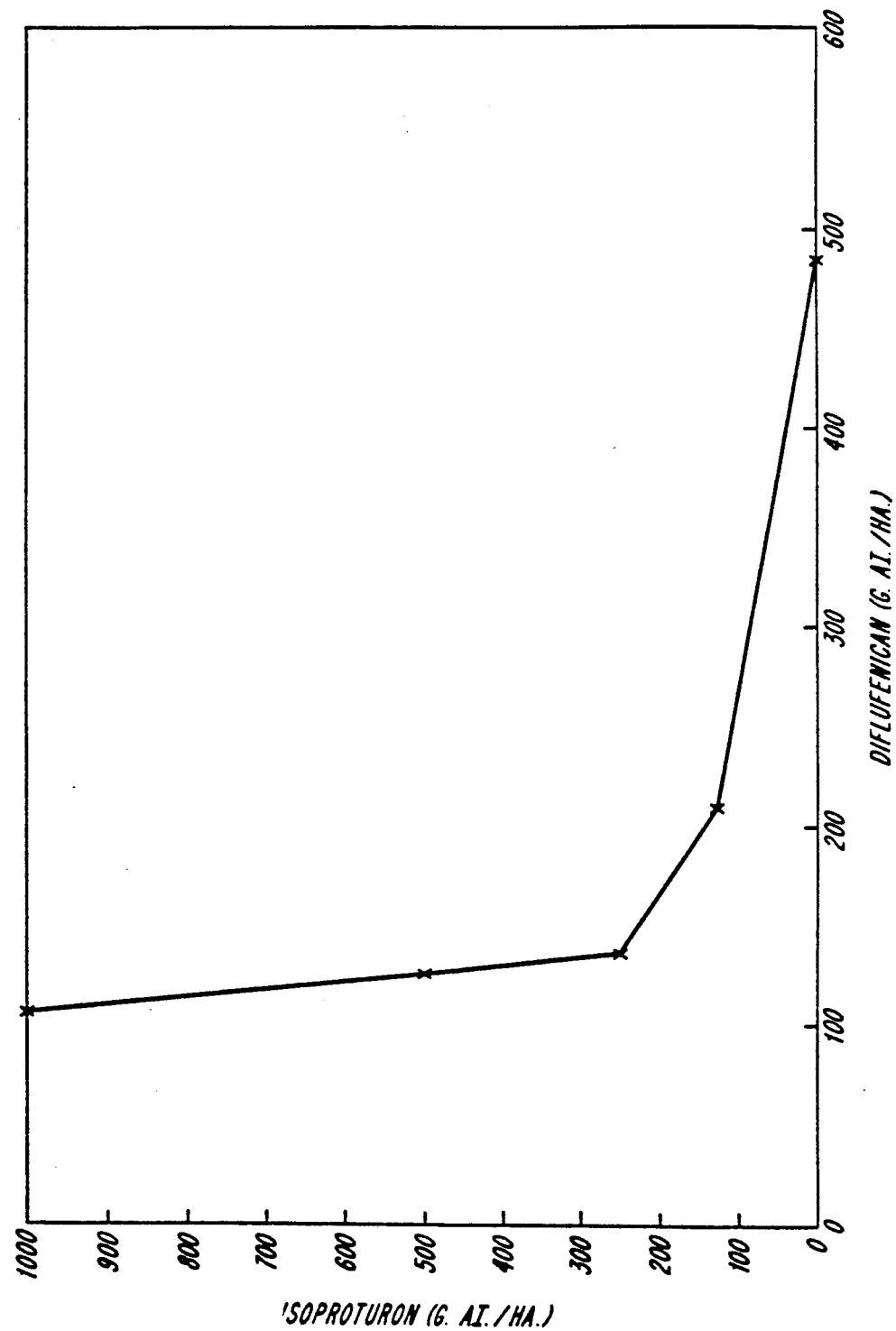

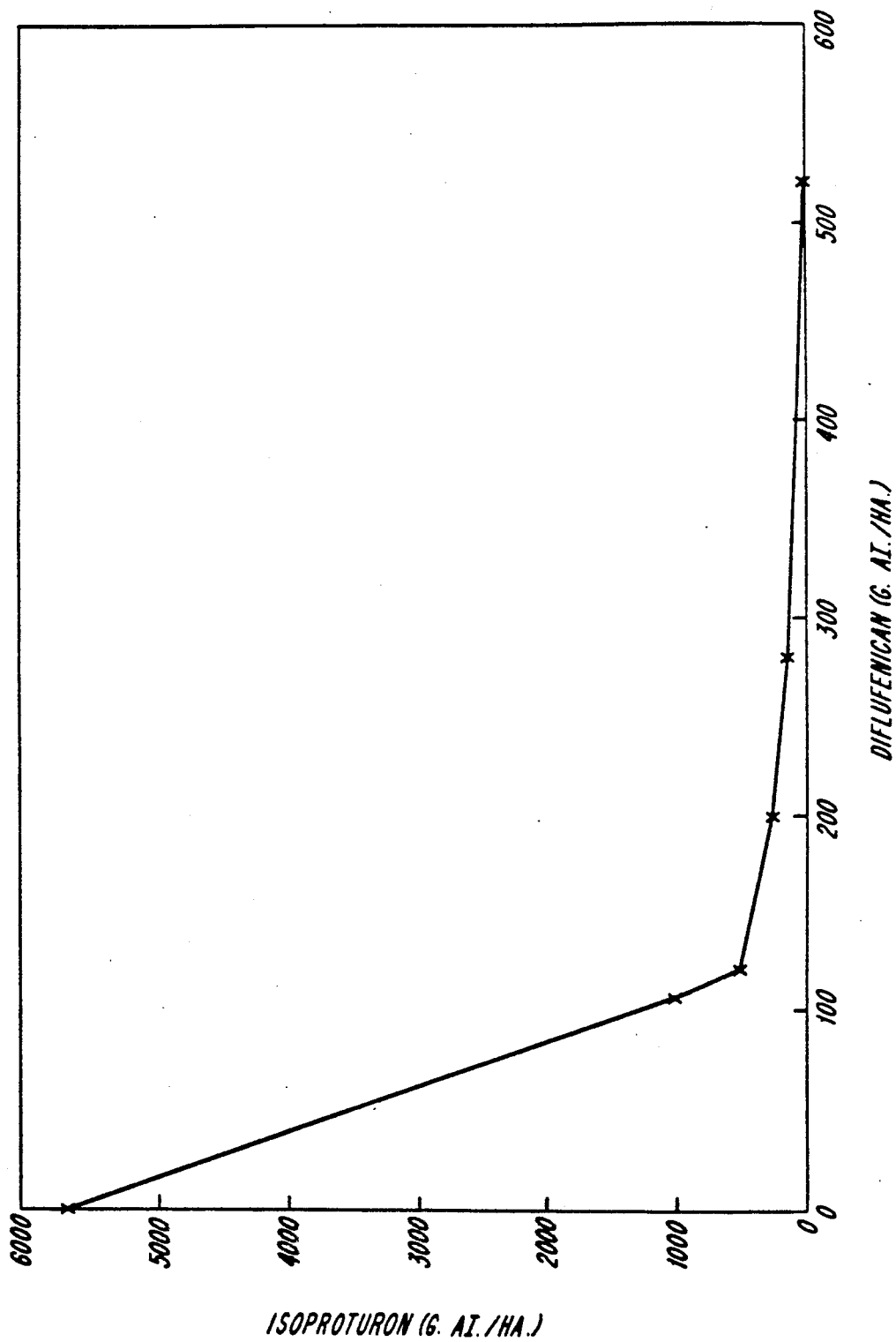

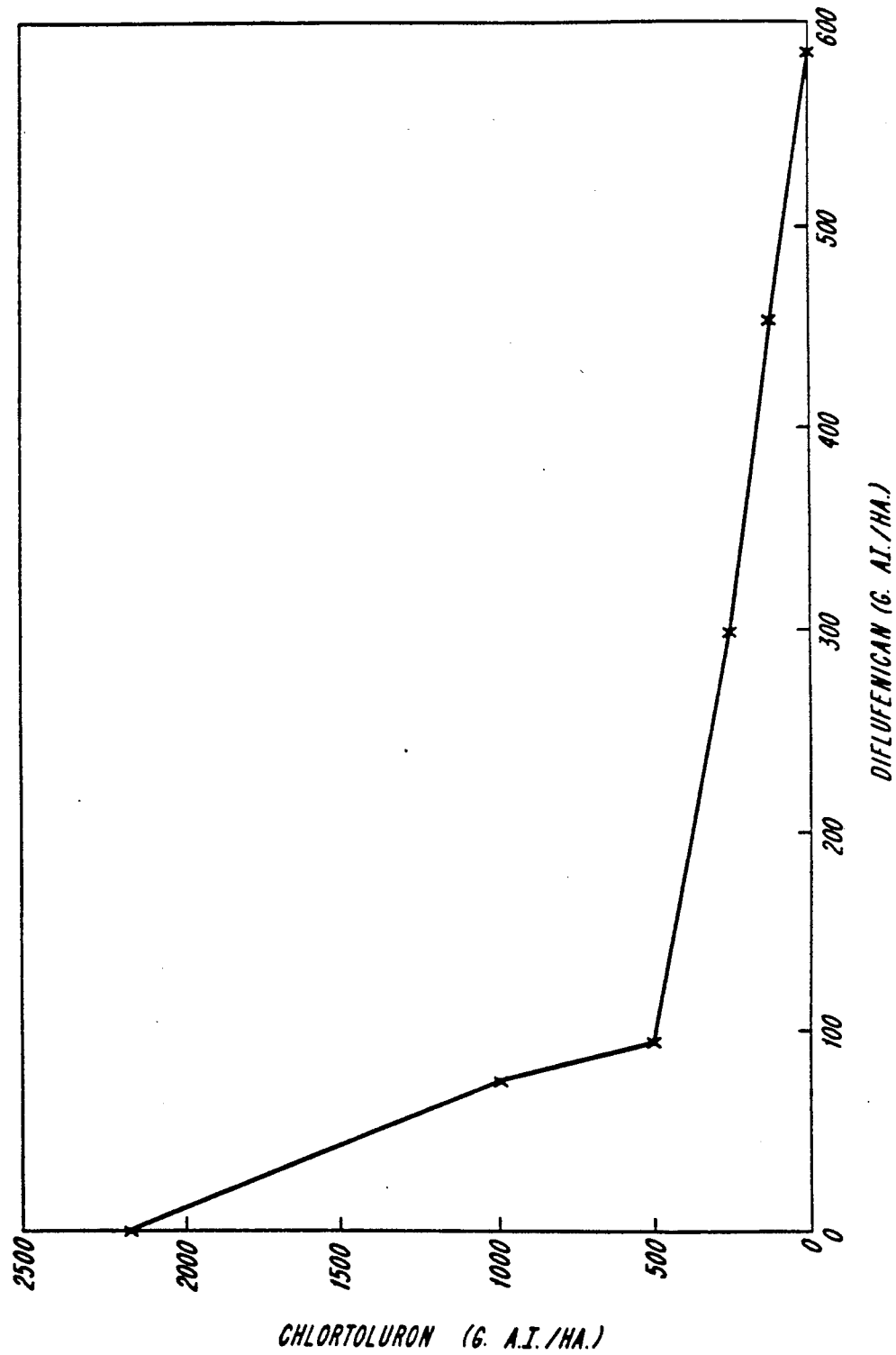

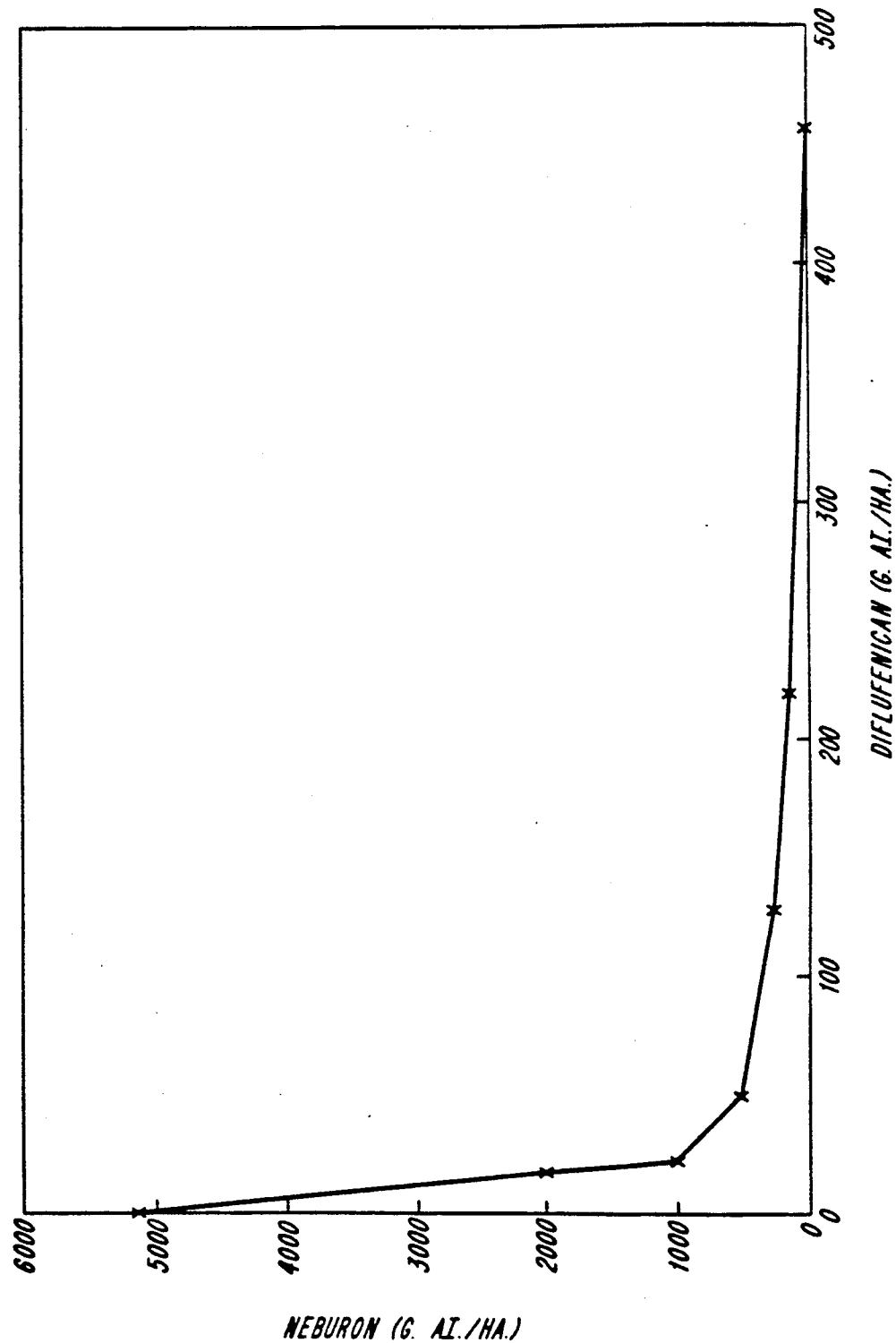

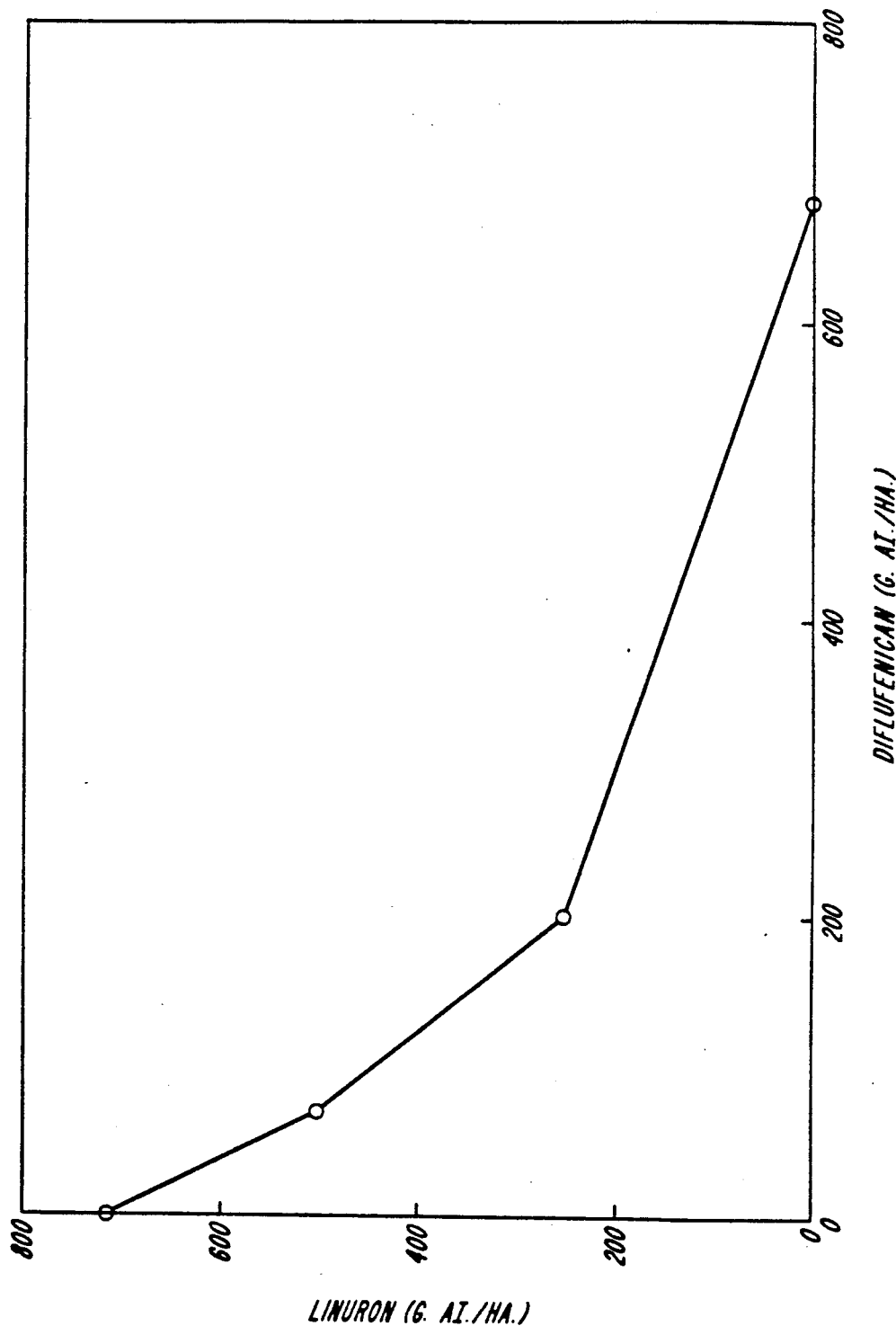

HERBICIDAL METHOD USING DIFLUFENICAN

This application is a divisional of application Ser. No. 881,006 filed Jul. 1, 1986.

The present invention relates to new herbicidal compositions comprising N-(2,4-difluorophenyl)-(2-(3-tri-fluromethylphenoxy) nicotinamide of the formula depicted in FIG. 1 hereinafter, which is disclosed in the specification of British Patent Publication No. 2087887A as a pre- and/or post-emergence herbicide, and to their use in agriculture.

The extensive use of the urea herbicides and mixtures thereof by which certain weed species such as *Galium aparine, Veronica hederifolia, Veronica persica* and *Viola arvensis* are poorly controlled, has led to an increase in the population of *Galium aparine*, Veronica and Viola, such that they now constitute a serious weed problem in cereal growing.

As a result of research and experimentation it has been discovered that the use of the compound N-(2,4-difluorophenyl)-2-(3-trifluoromethylphenoxy) nicotinamide (hereinafter referred to for convenience as diflufenican) in combination with the urea herbicide extends its spectrum of activity to include the control of *Galium aparine*, Veronica spp., and Viola spp. Therefore the said combined use represents an important technological advance.

Surprisingly, in addition to this, it has been found that the combined herbicidal activity of diflufenican with the urea herbicide against certain weed species is much greater than expected when applied pre- or post-emergence (e.g. as a pre- or post-emergence spray), i.e. the herbicidal activity of diflufenican with the urea herbicide showed an unexpected and remarkable degree of synergism as defined by P.M.L. Tammes, Netherlands Journal of Plant Pathology, 70 (1964), pp. 73–80 in a paper entitled "Isoboles, a graphic representation of synergism in pesticides", or as defined by Limpel, L.E., P.H. Schuldt and D. Lamont, 1962, Proc. NEWCC 16:48–53, using the formula $$E = X + Y - \frac{XY}{100}$$

where
E = the expected percent inhibition of growth by a mixture of two herbicides at defined doses.
X = the percent inhibition of growth by herbicide A at a defined dose
Y = the percent inhibition of growth by herbicide B at a defined dose
(when the observed response is greater than expected the combination is synergistic).

The remarkable synergism on *Galium aparine* and *Avena fatua* gives improved reliability of control of two of the most competitive weeds in cereal culture and leads to a considerable reduction in the amount of active ingredient required for weed control.

A high level of control of these species is desirable to prevent (a) loss of yield, through competition or difficulties with harvesting and seed cleaning and (b) to prevent unacceptable weed seed return to the soil.

It is to be understood that where in this specification reference is made to "the urea herbicide" it is intended to refer also to mixtures thereof where the context so permits. 2:1–1:2 wt/wt Mixtures, and more especially the 1:1 wt/wt mixtures, of isoproturon and neburon are preferred.

Accordingly the present invention provides a method for controlling the growth of weeds (i.e. undesired vegetation) at a locus which comprises applying to the locus amounts of (a) a urea herbicide, preferably a compound of the general formula:

$$R^1N(R^2)CON(R^3)R^4 \qquad \text{I}$$

wherein $R^1$ represents an optionally substituted cyclic hydrocarbyl (which is preferably aromatic e.g., phenyl) or aromatic heterocyclyl (e.g. benzothiazol-2-yl) group, $R^2$ represents the hydrogen atom or a straight or branched chain alkyl group containing from 1 to 6 carbon atoms, $R^3$ represents a straight or branched chain alkyl group containing from 1 to 6 carbon atoms or an optionally substituted cyclic hydrocarbyl (e.g., 2-methylcyclohexyl) group and $R^4$ represents the hydrogen atom or a straight or branched chain alkyl or alkoxy group containing from 1 to 6 carbon atoms, and (b) diflufenican, which are herbicidally effective in combination. For this purpose, the urea herbicide and diflufenican are normally used in the form of herbicidal compositions (i.e., in association with compatible diluents or carriers and/or surface-active agents suitable for use in herbicidal compositions), for example as hereinafter described.

Preferred compounds of general formula I are those wherein $R^2$ represents the hydrogen atom or the methyl group and $R^3$ represents the methyl group.

Compounds of general formula I wherein $R^1$ represents a phenyl group optionally substituted in the 3 and/or 4 positions relative to the nitrogen atom by a chlorine or bromine atom or by an optionally halogen-substituted straight- or branched-chain alkyl- or alkoxy group containing from 1 to 6 carbon atoms or by a similarly optionally substituted phenoxy group or represents the benzothiazol-2-yl group are also preferred.

Especially preferred compounds of general formula I are those wherein R2 represents the hydrogen atom, $R^3$ represents the methyl group and (a) $R^1$ represents a phenyl, 3-trifluoromethylphenyl or 4-chlorophenyl group and $R^4$ represents the methyl group; or (b) $R^1$ represents a 4-chlorophenyl group and $R^4$ represents the methoxy group, which are known respectively as fenuron, fluometuron, monuron and monolinuron, and more especially compounds of general formula I wherein $R^2$ represents the hydrogen atom and $R^3$ represents the methyl group and (c) $R^1$ represents a 3-chloro-4-methylphenyl or 4-isopropylphenyl group and $R^4$ represents the methyl group; or (d) $R^1$ represents the 3,4-dichlorophenyl group and $R^4$ represents a methyl, methoxy or butyl group ; or (e) $R^1$ represents the benzothiazol-2-yl group, $R^2$ represents the methyl group and $R^3$ represents the methyl group and $R^4$ represents the hydrogen atom, which are known respectively as chlortoluron, isoproturon, diuron, linuron, neburon and methabenzthiazuron.

The amounts of the urea herbicide and diflufenican applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between 150 g and 10 kg of the urea herbicide and between 25 g and 750 g of diflufenican per hectare give good results. However, it is to be understood that higher or lower application rates may be used, depending upon the particular problem of weed control encountered.

The urea herbicide and diflufenican in combination may be used to control selectively the growth of weeds, for example to control the growth of those species hereinafter mentioned, by pre- or post-emergence application in a directional or non-directional fashion, e.g. by directional or non-directional spraying, to a locus of weed infestation which is an area used, or to be used, for growing crops, for example cereals, e.g., wheat, barley, oats, rye, maize and rice, soya beans, field and dwarf beans, peas, lucerne, cotton, peanuts, flax, onions, carrots, oilseed rape, sunflower, and permanent or sown grassland before or after sowing of the crop or before or after emergence of the crop. For the selective control of weeds at a locus of weed infestation which is an area used, or to be used, for the growing of crops, e.g. the crops hereinbefore mentioned, application rates between 150 g and 3500 g of the urea herbicide and between 25 g and 250 g of diflufenican per hectare are particularly suitable.

According to a feature of the present invention, there is provided a method for the control of the growth of weeds by pre- or post-emergence application which comprises the combined use of (a) a urea herbicide chosen from chlortoluron, isoproturon, linuron, methabenzthiazuron and neburon or mixtures, preferably 2:1–1:2 wt/wt mixtures, thereof, for example 2:1–1:2 wt/wt mixtures (and more especially the 1:1 wt/wt mixture) of isoproturon and neburon, and (b) diflufenican at application rates of between 500 and 3500 g/ha, preferably between 500 and 2500 g/ha, and between 50 and 250 g/ha respectively, of (a) and (b) in proportions of 70:1 to 2:1 and preferably 50:1 to 2:1 wt/wt of (a) to (b), to control a very wide spectrum of annual broad-leafed weeds and grass weeds in cereal crops, e.g. wheat, barley, oats and rye, without significant permanent damage to the crop. The combined use described above offers both foliar and residual activity and consequently can be employed over a long period of crop development, i.e., from pre-weed pre-crop emergence to post-weed post-crop emergence. In the method according to this feature of the present invention, application of the herbicides to control weeds in autumn-sown cereals is preferred.

In the method described above, the combined use of (a) a urea herbicide chosen from chlortoluron, isoproturan and neburon or 2:1–1:2 wt/wt mixtures thereof and (b) diflufenican in proportions of 20:1 to 4:1 wt/wt of (a) to (b) is preferred.

The urea herbicide and diflufenican in combination may also be used to control the growth of weeds, especially those indicated below, by pre- or post-emergence application in established orchards and other tree-growing areas, for example forests, woods and parks, and plantations e.g. sugar cane, oil palm and rubber plantations. For this purpose they may be applied in a directional or non-directional fashion (e.g. by directional or non-directional spraying) to the weeds or to the soil in which they are expected to appear, before or after planting of the trees or plantations at application rates between 1000 g and 5000 g of the urea herbicide and between 100 g and 500 g of diflufenican per hectare.

The urea herbicide and diflufenican in combination may also be used to control the growth of weeds, especially those indicated below, at loci which are not crop-growing areas but in which the control of weeds is nevertheless desirable. Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought. Pre- or post-emergence application, and preferably pre-emergence application, in a directional or non-directional fashion (e.g., by directional or non-directional spraying) at application rates between 2500 g and 10 kg of the urea herbicide and between 200 g and 750 g of diflufenican per hectare are particularly suitable for this purpose.

By the term 'pre-emergence application' is meant application to the soil in which the weed seeds or seedlings are present before emergence of the weeds above the surface of the soil. By the term 'post-emergence application' is meant application to the aerial or exposed portions of the weeds which have emerged above the surface of the soil. By the term 'foliar activity' is meant herbicidal activity produced by application to the aerial or exposed portions of the weeds which have emerged above the surface of the soil. By the term 'residual activity' is meant herbicidal activity produced by application to the soil in which weed seeds or seedlings are present before emergence of the weeds above the surface of the soil, whereby seedlings present at the time of applicaton or which germinate subsequent to application from seeds present in the soil, are controlled.

Weeds that may be controlled by the method include:

| | |
|---|---|
| Veronica persica | Spergula arvensis |
| Veronica hederifolia | Cerastium holosteoides |
| Stellaria media | Arenaria serpyllifolia |
| Lamium purpureum | Silene vulgaris |
| Lamium amplexicaule | Legousia hybrida |
| Aphanes arvensis | Geranium molle |
| Galium aparine | Geranium dissectum |
| Alopecurus myosuroides | Erysimum cheiranthoides |
| Matricaria inodora | Descurainea sophia |
| Matricaria matricoides | Montia perfoliata |
| Anthemis arvensis | Anagallis arvensis |
| Anthemis cotula | Myosotis arvensis |
| Papaver rhoeas | Chenopodium album |
| Poa annua | Polygonum aviculare |
| Apera spica venti | Polygonum convolvulus |
| Phalaris paradoxa | Galeopsis tetrahit |
| Phalaris minor | Chrysanthemum segetum |
| Avena fatua | |
| Lolium perenne | |
| Lolium multiflorum | |
| Bromus sterilis | |
| Poa trivialis. | |

The pattern of persistence of the urea herbicide and the diflufenican allow the method of the present invention to be practised by the time-separated application of separate formulations.

In accordance with usual practice, a tank mix may be prepared prior to use by combining separate formulations of the individual herbicidal components.

The following Experiments illustrate the present invention:

EXPERIMENT 1

The following greenhouse experiment demonstrates the synergistic activity of the combined use of isoproturon and diflufenican in controlling the growth of certain weeds.

Greenhouse experiment showing nature of biological synergism between isoproturon and diflufenican A factorial experiment with 25 treatments was carried out to investigate the interaction of isoproturon and diflufenican at a wide range of doses, i.e., 0, 125, 250, 500 and 1000 g a.i./ha of isoproturon plus diflufenican at 0, 125, 250, 500 and 1000 g a.i./ha as indicated in the matrix below.

| | | isoproturon g a.i./ha | | | |
|---|---|---|---|---|---|
| Treatment diflufenican g a.i./ha | (1) 0 | (6) 125 | (11) 250 | (16) 500 | (21) 1000 |
| | (2) 125 | (7) 125 + 125 | (12) 250 + 125 | (17) 500 + 125 | (22) 1000 + 125 |
| | (3) 250 | (8) 125 + 250 | (13) 250 + 250 | (18) 500 + 250 | (23) 1000 + 250 |
| | (4) 500 | (9) 125 + 500 | (14) 250 + 500 | (19) 500 + 500 | (24) 1000 + 500 |
| | (5) 1000 | (10) 125 + 1000 | (15) 250 + 1000 | (20) 500 + 1000 | (25) 1000 + 1000 |

All treatmetns were made in an appropriate volume of water by mixing appropriate quantities of a 50% w/v aqueous suspension concentrate of isoproturon (commercial product) and diflufenican formulated as an experimental wettable powder (Example 1 hereinafter) containing 50% w/w active ingredient to give the above dose rates /ha in a spray volume of 260 l/ha. All treatments were applied using alaboratory sprayer fitted with a Sraying Systems Teejet SS 8003E operating at 2.1 kgf/cm$^2$. Treatmetns were appKed to 10–15 *Galium aparine* or *Avean fatua* seeds sown 1-2 cm deep in a loam soil in 9 cm diameter plastic pots.

There were 3 replicate pots per treatment arranged in a randomised block design. The pots were watered by a combination of overhead and sub-irrigation after treatment. A visual assessment of weed control was made 21 days after treatment using a 0-10 scale where 0=no activity and 10=100% control compared to the untreated plants.

The mean % weed control was calculated for each species and tabulated below for each treatment of the 25 treatments hereinbefore indicated.

| | Galium | | | | | Avena | | | |
|---|---|---|---|---|---|---|---|---|---|
| 0 | 0 | 0 | 0 | 0 | 0 | 43 | 50 | 67 | 70 |
| 47 | 80 | 87 | 90 | 93 | 50 | 70 | 83 | 90 | 93 |
| 70 | 90 | 100 | 100 | 100 | 80 | 90 | 93 | 97 | 100 |
| 80 | 100 | 100 | 100 | 100 | 90 | 97 | 97 | 100 | 100 |
| 100 | 100 | 100 | 100 | 100 | 95 | 100 | 100 | 100 | 100 |

From these results the 90% herbicidally effective dose (ED90) in g a.i./ha was calculated for diflufenican alone and isoproturon alone and diflufenican +125 g, 250 g, 500 g and 1000 g of isoproturon from the dose response curves.

| Galium (ED90 g/ha) | | Avena (ED90 g/ha) | |
|---|---|---|---|
| Diflufenican alone | 484 | Diflufenican alone | 538 |
| Diflufenican + 125 g/ha isoproturon | 209 | Diflufenican + 125 g/ha isoproturon | 275 |
| Diflufenican + 250 g/ha isoproturon | 136 | Diflufenican + 250 g/ha isoproturon | 199 |
| Diflufenican + 500 g/ha isoproturon | 125 | Diflufenican + 500 g/ha isoproturon | 122 |
| Diflufenican + 1000 g/ha isoproturon | 106 | Diflufenican + 1000 g/ha isoproturon | 107 |
| Isoproturon alone | (no activity) | Isoproturon alone | 5668 |

The values given above were then used to plot ED90 isoboles for (a) a "one sided effect" (Tammes p. 74 FIG. 1) in the case of Galium which was resistant to isoproturon, which is depicted in FIG. (i) hereinafter and (b) a "two sided effect" (Tammes p.75 FIG. 2) in the case of Avena where both compounds were active, which is depicted in FIG. (ii) hereinafter FIGS. (i) and (ii) clearly demonstrate type II and III isoboles respectively, which are characteristic of synergism.

ED90s were used for the construction of isoboles as 90% represents the desired level of weed control in an agricultural situation (see isobole for amitrole/atrazine synergism, Tammes FIG. 5 p. 77).

EXPERIMENT 2

A similar experiment to that hereinbefore described in Experiment 1 was carried out with chlortoluron and diflufenican against *Avena fatua* and gave the following results:

| | ED 90 (g/ha) |
|---|---|
| Diflufenican alone | 586 g/ha |
| Diflufenican + 125 g/ha chlortoluron | 450 g/ha |
| Diflufenican +·250 g/ha chlortoluron | 300 g/ha |
| Diflufenican + 500 g/ha chlortoluron | 95 g/ha |
| Diflufenican + 1000 g/ha chlortoluron | 75 g/ha |
| Chlortoluron alone | 2186 g/ha |

These results, plotted in FIG. (iii) hereinafter, for a "two sided effect" (Tammes p.75 FIG. 2) clearly demonstrate a type III isobole characteristic of synergism.

EXPERIMENT 3

Greenhouse experiment showing nature of biological synergism between neburon and diflufenican A factorial experiment with 43 treatments was carried out to investigate the interaction of neburon and diflufenican at a wide range of doses, i.e., 0, 125, 250, 500, 1000, 2000 and 4000 g a.i./ha of neburon plus diflufenican at 0, 31.25, 62.5, 125, 250, 500 and 1000 g a.i./ha as indicated in the matrix below.

| | | | Treatments: | | | | |
|---|---|---|---|---|---|---|---|
| | | | neburon g a.i./ha | | | | |
| diflufenican g a.i./ha | (1) 0 | (2) 125 | (3) 250 | (4) 500 | (5) 1000 | (6) 2000 | (7) 4000 |
| | (8) 31.25 | (9) 125 + 31.25 | (10) 250 + 31.25 | (11) 500 + 31.25 | (12) 1000 + 31.25 | (13) 2000 + 31.25 | — |

-continued

| | | | Treatments: | | | |
|---|---|---|---|---|---|---|
| | | | neburon g a.i./ha | | | |
| (14) | (15) | (16) | (17) | (18) | (19) | — |
| 62.5 | 125 + 62.5 | 250 + 62.5 | 500 + 62.5 | 1000 + 62.5 | 2000 + 62.5 | |
| (20) | (21) | (22) | (23) | (24) | (25) | — |
| 125 | 125 + 125 | 250 + 125 | 500 + 125 | 1000 + 125 | 2000 + 125 | |
| (26) | (27) | (28) | (29) | (30) | (31) | — |
| 250 | 125 + 250 | 250 + 250 | 500 + 250 | 1000 + 250 | 2000 + 250 | |
| (32) | (33) | (34) | (35) | (36) | (37) | — |
| 500 | 125 + 500 | 250 + 500 | 500 + 500 | 1000 + 500 | 2000 + 500 | |
| (38) | (39) | (40) | (41) | (42) | (43) | — |
| 1000 | 125 + 1000 | 250 + 1000 | 500 + 1000 | 1000 + 1000 | 2000 + 1000 | |

All treatments were made in an appropriate volume of water to give the above dose rates/hectare in a spray volume of 290 l/ha. The neburon was formulated as an experimental 25% w/w wettable powder (Example 9 hereinafter). The diflufenican was an experimental aqueous suspension concentrate (Example 2 hereinafter) containing 50% w/v active ingredient. All treatments were applied using a laboratory sprayer fitted with a Spraying Systems Teejet SS 8003E operating at 2.95 kgf/cm$^2$.

Treatments were applied post-emergence to *Galium aparine* at the 2 whorls growth stage. Plants were grown in non-sterile clay loam in 7 cm square plastic pots. There were four replicated pots per treatment and these were arranged in randomised blocks in the glasshouse. The pots were watered by a combination of overhead and sub-irrigation after treatment.

A visual assessment of weed control on a 0-100 scale was made 22 days after treatment. The mean % weed control was calculated for each treatment for each species. From these results the 90% herbicidally effective dose (ED 90) in g ai/ha was calculated for diflufenican alone, neburon alone and for diflufenican +125, 250, 500, 1000 and 2000 g a.i./ha neburon from the dose response curves for *Galium aparine*.

| Galium (ED90 g/ha) | |
|---|---|
| Diflufenican alone | 459 |
| Diflufenican + 125 g/ha neburon | 218 |
| Diflufenican + 250 g/ha neburon | 127 |
| Diflufenican + 500 g/ha neburon | 49 |
| Diflufenican + 1000 g/ha neburon | 22 |
| Diflufenican + 2000 g/ha neburon | 15 |
| Neburon alone | 5185 |

The ED90 values were used to plot a "two sided effect" isobole for Galium given in FIG. (iv) hereinafter. The isobole was of type III clearly demonstrative of synergism (Tammes, p. 75 FIG. 2). EXPERIMENT 4

Greenhouse experiment showing the nature of biological synergism between linuron and diflufenican A similar experiment to that hereinbefore described in Experiment 3 was carried out with linuron and diflufenican using 0, 250, 500, 1000 and 2000 g a.i./ha of linuron formulated as a 50% w/w wettable powder (commercial product) plus diflufenican at 31, 125, 500 and 1000 g a.i./ha. The following ED$_{90}$ values were computed from the results.

| | ED$_{90}$ g/ha |
|---|---|
| Diflufenican alone | 684 |
| Diflufenican + linuron 250 g/ha | 201 |
| Diflufenican + linuron 500 g/ha | 69 |
| Diflufenican + linuron 1000 g/ha | less than 31 |
| Diflufenican + linuron 2000 g/ha | less than 31 |

The results, plotted in FIG. (v) hereinafter for a "two sided effect" (Tammes, p 75, FIG. 2) clearly demonstrate a type III isobole characteristic of synergism.

EXPERIMENT 5

Greenhouse experiment showing the nature of biological synergism between diuron and diflufenican A similar experiment to that hereinbefore described in Experiment 3 was carried out with diuron and diflufenican using 0 and 187.5 g a.i./ha of diuron formulated as an 80% w/w wettable powder (commercial product) plus diflufenican at 31, 63, 125, 250, 500 g a.i./ha.

The observed weed control results are compared with the expected result using the Limpel formula :

$$E = X + Y - \frac{XY}{100} \text{ below:}$$

| | | Diuron g/ha | |
|---|---|---|---|
| % control | | 0 | 187.5 |
| | | Observed | Expected (E) |
| | 0 | — | 60 | — |
| | 31 | 43 | 93 | 78 |
| Diflufenican g/ha | 63 | 68 | 100 | 87 |
| | 125 | 73 | 100 | 89 |
| | 250 | 83 | 100 | 93 |
| | 500 | 85 | 99 | 94 |

As the observed responses with the mixtures were higher than the expected figures the combinations were clearly synergistic.

EXPERIMENT 6

The efficacy of these synergistic mixtures for broad spectrum weed control in cereals was demonstrated in a series of small plot field trials where mixtures of diflufenican (Example 2 hereinafter) and isoproturon were compared to isoproturon alone.

The treatments were applied pre- or post-emergence to three replicate 6 m × 3 m randomised plots at a total of 21 field sites in a volume of 141 liters/ha using a motorised small plot spraying machine fitted with 6 × 80015 Spraying Systems Teejets. Mixtures were achieved by spraying the plots with each component separately within minutes of each other (i.e. total volume of 282 l/ha).

Weed control was assessed after 3 months by counting the number of weeds in 2 × 0.5 m$^2$ quadrats per plot. Crops were assessed for any visual phytotoxicity on a scale of 0-100, where 0 = no damage and 100 = 100% kill.

The results are shown in Table I below.

TABLE I

| Treatment | | Am | Pa | Ga | Vp | Vh | Va | Lp | Sm | Mi | Pr | Aa | Ba | Whe |
|---|---|---|---|---|---|---|---|---|---|---|---|---|---|---|
| Isoproturon | (a) | 93(3) | 84(5) | 31(4) | 24(6) | 13(1) | 26(5) | 31(2) | 83(6) | 99(3) | 100(1) | 100(1) | 2(4) | 1(6) |
| 2000 g/ha | (b) | 88(4) | — | 0(2) | 60(4) | — | — | — | 100(2) | 100(2) | — | — | 2(4) | 1(2) |
| Isoproturon | (a) | 100(3) | 99(5) | 83(4) | 100(6) | 100(1) | 98(5) | 100(2) | 100(6) | 100(3) | 100(1) | 100(1) | 4(5) | 2(6) |
| 1500 g/ha + diflufenican 125 g/ha | (b) | 93(3) | — | 86(2) | 100(4) | — | — | — | 100(2) | 100(2) | — | — | 3(4) | 1(2) |
| Isoproturon | (a) | 100(3) | 100(5) | 99(4) | 100(6) | 100(1) | 95(5) | 99(2) | 100(6) | 100(3) | 100(1) | 100(1) | 8(4) | 5(6) |
| 1500 g/ha + diflufenican 250 g/ha | (b) | 93(3) | — | 99(4) | 100(4) | — | — | — | 100(2) | 100(2) | — | — | 4(4) | 2(2) |

Suffix in parentheses = no. of occurrences
*mean % crop phytotoxicity (highest recorded)
Am = Alopecurus myosuroides
Pa = Poa annua
Ga = Galium aparine
Vp = Veronica persica
Vh = Veronica hederifolia
Va = Viola arvensis
Lp = Lamium purpureum
Sm = Stellaria media
Mi = Matricaria inodora
Pr = Papaver rhoeas
Aa = Aphanes arvensis
Ba = barley
Wh = wheat
(a) = Pre-emergence
(b) = Post-emergence

EXPERIMENT 7

The efficacy of these synergistic mixtures for broad spectrum weed control in cereals was demonstrated in a series of small plot field trials where tank mixtures of diflufenican (Example 2 hereinafter) and chlortoluron were compared with diflufenican alone.

The treatments were applied pre-emergence to three replicate 6 m × 3 m randomised plots at six field sites in a volume of 261 l/ha using a motorised small plot spraying machine fitted with 6 × 8004 Spraying Systems Tee Jets.

Weed control was assessed in the spring following autumn application by ounting the number of weeds in 3 × 0.5 m² quadrats per plot. Crops were assessed for any visual phytotoxicity on a scale of 0-100 where 0 = no damage and 100 = 100% kill.

The results are shown in Table II below.

TABLE II

| Treatment | mean percentage control of weed numbers | | | | | | | | | | Winter* | | |
|---|---|---|---|---|---|---|---|---|---|---|---|---|---|
| | An.a | Aa | As | Cs | La | Pr | Rr | Sm | Mi | Vp | Wh | Ba | Rye |
| Chlortoluron 1500 g/ha + diflufenican 6.25 g/ha | 100(1) | 100(1) | 100(1) | 99(1) | 99(1) | 99(2) | 99(1) | 99(3) | 99(2) | 99(1) | 0(1) | 5.7(4) | 0(1) |
| Diflufenican 125 g/ha | 100(1) | 100(1) | 100(1) | 0(1) | 99(1) | 72(2) | 100(1) | 99(3) | 99(2) | 99(1) | 0(1) | 3.7(4) | 0(1) |

Suffix in parentheses = number of occurrences.
*mean % crop phytotoxicity (highest recorded).
An.a = Anagallis arvensis
As = Arenaria serpyllifolia
Cs = Chrysanthemum segetum
La = Lamium amplexicaule
Rr = Raphanus raphanistrum

EXPERIMENT 8

Field trials were carried out in Belgium with tank-mixtures of diflufenican (Example 2 hereinafter) with isoproturon:neburon (1:1) or methabenzthiazuron. The treatments were applied in the autumn pre-emergence to replicate 30 m² plots to control a range of broad leaf and grass weeds in winter wheat and winter barley in a volume of 500 l/ha using a hand held sprayer. Assessments of weed control were made in the spring following autumn application. Crop phytotoxicity was recorded during the winter and spring and the maximum recorded damage is given with the results shown in Table III below.

TABLE III

| | | mean % phytotoxicity | | | | | | Max. recorded phytotoxicity on wheat or barley |
|---|---|---|---|---|---|---|---|---|
| | | Am | Pa | Mi | Sm | Ga | V spp | Wheat/Barley |
| Diflufenican + neburon + isoproturon | 125 g/ha + 800 g/ha + 800 g/ha | 95(3) | 100(1) | 100(2) | 100(3) | 100(1) | 100(1) | 8(4) |
| Diflufenican + | 200 g/ha + | 93(4) | 99(1) | 100(3) | 100(4) | 97(2) | 100(1) | 10(4) |

TABLE III-continued

|  | mean % phytotoxicity | | | | | | Max. recorded phytotoxicity on wheat or barley |
|---|---|---|---|---|---|---|---|
|  | Am | Pa | Mi | Sm | Ga | V spp | Wheat/Barley |
| methabenzthiazuron 1750 g/ha | | | | | | | |

Suffix in parentheses = no. of occurrences
V spp = *Veronica spp*

These trials demonstrate clearly the wide spectrum of control include *Galium aparine*, Veronica and Viola which can be obtained with the mixtures.

According to a further feature of the present invention, there are provided compositions suitable for herbicidal use comprising (a) the urea herbicide and (b) diflufenican in proportions of preferably 400:1 to 1:5 wt/wt of (a) to (b) preferably 70:1 to 2:1 wt/wt of (a) to (b) and more preferably 20:1 to 4:1 wt/wt of (a) to (b)] in association with, and preferably homogeneously dispersed in, one or more compatible herbicidally-acceptable diluents or carriers and/or surface-active agents (i.e., diluents or carriers or surface-active agents of the type generally accepted in the art as being suitable for use in herbicidal compositions and which are compatible with the urea herbicide and diflufenican). The term "homogeneously dispersed" is used to include compositions in which the urea herbicide and diflufenican are dissolved in the other components. The term "herbicidal compositions" is used in a broad sense to include not only compositions which are ready for use as herbicides but also concentrates which must be diluted before use. Preferably, the compositions contain from 0.05 to 90% by weight of the urea herbicide and diflufenican.

The herbicidal compositions may contain both a diluent or carrier and a surface-active (e.g., wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with nonyl- or octyl-phenols, or carboxylic acid esters of anhydrosorbitols which have been rendered soluble by etherification of the free hydroxy groups by condensation with ethylene oxide, alkali and alkaline earth metal salts or sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates. Examples of suitable solid diluents or carriers are aluminium silicate, talc, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the urea herbicide and diflufenican with solid diluents or by impregnating the solid diluents or carriers with solutions of the urea herbicide and diflufenican in volatile solvents, evaporating the solvents and, if necessary, grinding the products so as to obtain powders. Granular formulations may be prepared by absorbing the urea herbicide and diflufenican (dissolved in volatile solvents) onto the solid diluents or carriers in granular form and evaporating the solvents, or by granulating compositions in powder form obtained as described above. Solid herbicidal compositions, particularly wettable powders, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, acetophenone, cyclohexanone, isophorone, toluene, xylene and mineral, animal and vegetable oils (and mixtures of these diluents). Surface-active agents, which may be present in the liquid compositions, may be ionic or non-ionic (for example of the types described above) and may, when liquid, also serve as diluents or carriers.

Wettable powders and liquid compositions in the form of concentrates may be diluted with water or other suitable diluents, for example mineral or vegetable oils, particularly in the case of liquid concentrates in which the diluent or carrier is an oil, to give compositions ready for use. When desired, liquid compositions of the urea herbicide and diflufenican may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Preferred herbicidal compositions according to the present invention are aqueous suspension concentrates which comprise from 10 to 70% w/v of the urea herbicide and diflufenican, from 2 to 10% w/v of surface-active agent, from 0.1 to 5% w/v of thickener and from 15 to 87.9% by volume of water; wettable powders which comprise from 10 to 90% w/w of the urea herbicide and diflufenican, from 2 to 10% w/w of surface-active agent and from 10 to 88% w/w of solid diluent or carrier; liquid water soluble concentrates which comprise from 10 to 30% w/v of the urea herbicide and diflufenican, from 5 to 25% w/v of surface-active agent and from 45 to 85% by volume of water-miscible solvent, e.g. dimethylformamide; liquid emulsifiable suspension concentrates which comprise 10 to 70% w/v of the urea herbicide and diflufenican, from 5 to 15% w/v of surface-active agent, from 0.1 to 5% w/v of thickener and from 10 to 84.9% by volume of organic solvent; granules which comprise from 2 to 10% w/w of the urea herbicide and diflufenican, from 0.5 to 2% w/w of surface-active agent and from 88 to 97.5% w/w of granular carrier and emulsifiable concentrates which comprise from 0.05 to 90% w/v, and preferably from 1 to 60% w/v, of the urea herbicide and diflufenican, from 0.01 to 10% w/v, and preferably from 1 to 10% w/v, of surface-active agent and from 9.99 to 99.94%, and preferably from 39 to 98.99%, by volume of organic solvent.

Herbicidal compositions according to the present invention may also comprise the urea herbicide and diflufenican in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled, for example alachlor [αchloro-2,6-diethyl-N-(methoxymethyl)acetanilide], asulam [methyl (4-aminobenzenesulphonyl)carbamate], alloxydim Na [sodium salt of 2-(1-allyloxyaminobutylidine) 5,5-dimethyl-4-methoxycarbonylcyclohexane-1,3-dione], atrazine (2-chloro-4-ethylamino-6-isopropylamino-1,3,5triazine], barban [4-chlorobut-2-ynyl N-(3chlorophenyl)carbamate], benzoylprop-ethyl [ethyl N-benzoyl-N-(3,4-dichlorophenyl-2-aminopropionate], bromoxynil [3,5-dibromo-4-hydroxy-benzonitrile](preferred), butachlor [N-(butoxymethyl)-αchloro-2,6-diethylacetanilide], butylate [S-ethyl N,N-diisobutyl(thiocarbamate)], carbetamide [D-N-ethyl-2-(phenyl carbamoyloxy)propionamide], chlorfenpropmethyl [methyl 2-chloro-2(4-chlorophenyl) propionate], chlorpropham [isopropyl N-(3-chlorophenyl)carbamate], cyanazine [2-chloro-4-(1-cyano-1-methylethylamino)-6-ethylamino-1,3,5-triazine], cycloate [N'-cyclohexyl-N-ethyl-S-ethyl acid (thiocarbamate)], 2,4D[2,4 -dichlorophenoxyacetic dalapon [2,2-dichloropropionic acid], 2,4-DB [4-(2,4-dichlorophenoxy)butyric acid], desmedipham [3-(ethoxycarbonylamino)phenyl N-phenylcarbamate], diallate [S-2,3-dichloroallyl-N,N-diisopropyl(thiocarbamate)], dicamba [3,6-dichloro-2methoxybenzoic acid], dichlorprop [(+)-2-(2,4-dichlorophenoxy)propionic acid], difenzoquat [1,2-dimethyl-3,5-diphenyl-pyrazolium salts], dinitramine ,N¹, N¹-diethyl2,6-dinitro-4-trifluoromethyl-m-phenylendiamine], EPTC [S-ethyl N,N-dipropyl(thiocarbamate), ethofumesate 2-ethoxy-2,3-dihydro-3,3-dimethyl-benzofuran-5-yl methylsulphonate], flamprop-isopropyl isopropyl (+)-2-(N-benzoyl-3-chloro-4fluoroanilino)propionate]flampropmethyl [methyl (±)-2-(N-benzoyl-3-chloro-4-fluoroanilino)propionate]ioxynil [4-hydroxy-3,5-di-iodobenzonitrile](preferred), MCPA [4-chloro-2-methylphenoxyacetic acid], MCPB [4-(4-chloro-2-methylphenoxy) butyric acid], mecoprop [(±)-2-(4-chloro-2-methyl-phenoxy) propionic acid](preferred), metamitron [4-amino-3-methyl-6-phenyl-1,2,4-triazin-5(4H)-one], metribuzin [4-amino-6-t-butyl-3-(methylthio)-1,2,4-triazin-5 (4H) -one], molinate [S-ethyl N,N-hexamethylene(thiocarbamate)], oxadiazon [3-(2,4-dichloro-5-isopropoxyphenyl)-5-t-butyl-1,3,4-oxadiazoline-2-one], paraquat [1,1'-dimethyl-4,4'-bipyridylium salts], pebulate [S-propyl N-butyl-N-ethyl (thiocarbamate)], phenmedipham [3-(methoxy-carbonylamino) phenyl N-(3-methylphenyl)carbamate], prometryne [4,6-bisisopropylamino-2-methylthio-1,3,5triazine]-propachlor [α-chloro-N-isopropylacetanilide], propanil [N-(3,4-dichlorophenyl)propionamide], propham [isopropyl N-phenylcarbamate], pyrazone [5-amino-4-chloro-2-phenylpyridazin-3(2H)one], simazine [2-chloro-4,6-bisethylamino-1,3,5triazine], TCA (trichloroacetic acid), thiobencarb [S-(4-chlorobenzyl)-N,N-diethylthiolcarbamate], triallate [S-2,3,3-trichloroallyl N,N-di-isopropyl(thiocarbamate)], and trifluralin [2,6-dinitro-N,N-dipropyl-4-trifluoromethylaniline]; insecticides, e.g. carbaryl [naphth-1-yl N-methylcarbamate]; synthetic pyrethroids, e.g. permethrin and cypermethrin; and fungicides, e.g. 2,6-dimethyl-4-tridecyl-morpholine, methyl N-(1-butylcarbamoyl-benzimidazol-2-yl) carbamate, 1,2-bis-(3-methoxy-carbonyl-2-thioureido) benzene, isopropyl 1-carbamoyl-3-(3,5-dichlorophenyl) hydantoin and 1-(4-chloro-phenoxy) 3,3-dimethyl-1-(1,2,4-triazol-1-yl)-butan-2one. Other biologically active materials which may be included in, or used in conJunction with, the herbicid-al compositions of the present invention are plant growth regulators, e.g. succinamic acid, (2-chloroethyl)trimethylammonium chloride and 2-chloroethane-phosphonic acid; or fertilizers, e.g., containing nitrogen, potassium and phosphorus and trace elements known to be essential to successful plant life, e.g. iron, magnesium, zinc, manganese, cobalt and copper.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

The compositions of the invention may be made up as an article of manufacture comprising the urea herbicide-and diflufenican and optionally other pesticidally active compounds as hereinbefore described or, as is preferred, a herbicidal composition as hereinbefore described, and preferably a herbicidal concentrate which must be diluted before use, comprising the urea herbicide and diflufenican within a container for the aforesaid urea herbicide and diflufenican or a said herbicidal composition, and instructions physically associated with the aforesaid container setting out the manner in which the aforesaid urea herbicide and diflufenican or herbicidal composition contained therein is to be used to control the growth of weeds. The containers will normally be of the types conventionally used for the storage of chemical substances which are solids at normal ambient temperatures and herbicidal compositions, particularly in the form of concentrates, for example cans and drums of metal, which may be internally-lacquered, and plastics materials, bottles of glass and plastics materials and, when the contents of the container is a solid, for example granular herbicidal compositions, boxes, for example of cardboard, plastics materials and metal, or sacks. The containers will normally be of sufficient capacity to contain amounts of the active ingredients or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 150 g and 10 kg of the urea herbicide and between 25 g and 750 g of diflufenican per hectare in the manner and for the purposes hereinbefore described.

According to a further feature of the present invention, there is provided a product comprising (a) a urea herbicide and (b) diflufenican as a combined preparation for simultaneous, separate or sequential use in controlling the growth of weeds at a locus.

The following Examples illustrate herbicidal compositions according to the present invention and herbicidal compositions suitable for use in the method for controlling the growth of weeds according to the present invention.

EXAMPLE 1

A wettable powder was formed thus:

| | |
|---|---|
| Diflufenican | 50% w/w |
| Nekal BX (sodium alkyl naphthalene sulphonate) | 10% w/w |
| Sodium lignosulphonate | 3% w/w |
| Sopropon T36 (sodium polycarboxylate) | 0.5% w/w |
| Hymod AT (ball clay) | to 100% w/w |

EXAMPLE 2

An aqueous suspension concentrate was formed from:

| | |
|---|---|
| Diflufenican | 50% w/v |
| Ethylan BCP (a nonylphenol-ethylene oxide condensate containing 9 moles of ethylene oxide per mole of phenol) | 0.5% w/v |
| Soprophor FL (triethanolamine salt of oxyethylated polyarylphenolphosphate) | 1.0% w/v |
| Sopropon T36 (sodium polycarboxylate) | 0.5% w/v |
| Antifoam FD | 0.1% w/v |
| Rhodigel 23 (xanthan gum) | 0.2% w/v |
| Dichlorophen sodium solution, 40% w/w | 0.25% w/v |
| Water | to 100% by volume |

EXAMPLE 3

A (20:1) wettable powder was formed from:

| | |
|---|---|
| Isoproturon | 40% w/w |
| Diflufenican | 2% w/w |
| Arylan S (sodium dodecyl benzene sulphonate) | 2% w/w |
| Darvan No. 2 (sodium lignosulphonate) | 5% w/w |
| Aerosil (silicon dioxide of microfine particle size) | 5% w/w |
| Celite PF (synthetic magnesium silicate carrier) | 46% w/w | by mixing the ingredients and grinding the mixture in a hammer mill to give a wettable powder which may be diluted with water and applied at a a rate of 6.25 kg per hectare in 200 liters of spray fluid per hectare to control a wide range of grass and broad-leaf weeds including *Avena fatua* and *Galium aparine*, by pre- or post-emergence application to a crop of winter wheat.

EXAMPLE 4

An (4:1) aqueous suspension concentrate was formed from

| | |
|---|---|
| Isoproturon | 40% w/v |
| Diflufenican | 10% w/v |
| Ethylan BCP (a nonylphenol-ethylene oxide condensate containing 9 moles of ethylene oxide per mole of phenol) | 2% w/v |
| Antifoam FD (silicone emulsion antifoaming agent) | 0.5% w/v |
| Pluronic L62 (an ethylene oxide/propylene oxide block co-polymer) | 2% w/v |
| Sopropon T36 (sodium salt of polycarboxylic acid) | 0.5% w/v |
| Attagel 50 (swelling attapulgite clay) | 0.5% w/v |
| Water | to 100% by volume | by intimately mixing the ingredients and grinding in a ball-mill for 24 hours. The concentrate thus obtained may be dispersed in water and applied at an application rate of 2 liters per hectare pre- or post-emergence to a crop of barley to control a wide range of broad leaf weeds, including *Galium aparine*.

EXAMPLE 5

A (20:1) water dispersible granule form was formed by granulating the ingredients used in Example 3 with water using a pan granulator into granules of 0.1-2 mm diameter. These granules can then be dispersed at a rate of 6.25 kg in 200 liters of water per hectare to control a wide range of grass and broad-leaf weeds by pre- or post-emergence application to a crop of winter wheat.

Example 6

An (50:1) emulsifiable suspension concentrate was formed from:

| | |
|---|---|
| Isoproturon | 50% w/v |
| Diflufenican | 1% w/v |
| Ethylan TU (a nonyl phenol/ethylene oxide condensate containing 10 moles of ethylene oxide per mole of phenol) | 10% w/v |
| Bentone 38 (an organic derivative of special magnesium montmorillonite thickener) | 0.5% w/v |
| Aromasol H (an aromatic solvent consisting predominantly of isomeric trimethylbenzenes) | to 100% by volume | by intimately mixing the ingredients and grinding in a ball-mill for 24 hours. The emulsifiable suspension concentrate thus obtained may be diluted with water and applied at an application rate of 5 liters of emulsifiable suspension concentrate in 100 liters of spray fluid per hectare to control the growth of *Alopecurus myosuroides*, *Viola arvensis* and *Veronica persica* prior to the emergence of a crop of winter wheat.

EXAMPLE 7

A (1:2) tank mix of (a) the aqueous suspension concentrate of diflufenican (Example 2) and a 50% w/v commercial formulation of isoproturon (b) was prepared by adding 0.5 liters of (a) to 1 liters of (b) in 200 liters of water. The resulting spray fluid was applied to one hectare of wheat soon after emergence of the crop and weeds to control *Galium aparine, Viola arvensis, Veronica hederifolia, Veronica persica, Stellaria media* and *Matricaria inodora*.

EXAMPLE 8

A (1:70) tank mix of (a) the aqueous suspension concentrate of diflufenican (Example 2) and a 50% w/v commercial formulation of chlortoluron (b) was prepared by adding 0.1 liters of (a) to 7 liters of (b) in 200 liters of water. The resulting spray fluid was applied to one hectare of wheat soon after emergence of crop and weeds to control *Avena fatua, Alopecurus myosuroides, Stellaria media, Matricaria inodora, Veronica persica* and *Viola arvensis.*

EXAMPLE 9

A wettable powder was formed thus:

| | |
|---|---|
| Neburon | 25% w/w |
| Nekal BX (sodium alkyl naphthalene sulphonate | 10% w/w |
| Sodium lignosulphonate | 3% w/w |
| Sopropon T36 (sodium polycarboxylate) | 0.5% w/w |
| Silica filler | to 100% w/w |

EXAMPLE 10

A (1.25:16) tank mix of (a) the aqueous suspension concentrate of diflufenican (Example 2) and a 50% w/w commercial formulation of isoproturon:neburon (1:1) (b) was prepared by adding 0.25 liters of (a) to 3.2 kg of (b) in 200 liters of water. The resulting spray fluid was applied to one hectare of wheat soon after emergence of crop and weeds to control *Avena fatua, Alopecurus myosuroides, Stellaria media, Matricaria inodora, Veronica persica* and *Viola arvensis.*

EXAMPLE 11

A (1:8.75) tank mix of (a) the aqueous suspension concentrate of diflufenican (Example 2) and a 70% w/w commercial formulation of methabenzthiazuron (b) was prepared by adding 0.4 liters of (a) to 2.5 kg of (b) in 200 liters of water. The resulting spray fluid was applied to one hectare of wheat soon after emergence of crop and weeds to control *Avena falua Alopecurus myosuroides, Stellaria media, Matricaria inodora, Veronica persica* and *Viola arvensis.*

In the mixed formulations in the Examples hereinbefore, the urea herbicide may be replaced by one other or a mixture of the urea herbicides.

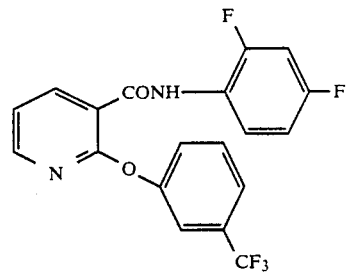

Figure I

We claim:

1. A packaged product comprising an effective amount of
   (a) at least one urea herbicide of the general formula $$R^1N(R^2)CON(R^3)R^4 \qquad I$$

wherein $R^2$ represents a hydrogen atom;
   $R^3$ represents a methyl group;
   $R^1$ represents a 3-chloro-4-methylpheny or 4-isopropylphenyl group and $R^4$ represents methyl group, or $R^1$ represents a 3,4-dichlorophenyl group and $R^4$ represents a methyl, methoxy or butyl group; and
   (b) diflufenican,
   in which the packed ratio of (a) to (b) ranges from 400:1 to 1:5 by weight and the components (a) and (b) are capable of controlling the growth of weeds at a locus.

2. The product of claim 1, wherein the packed ratio of (a) to (b) ranges from about 20:1 to 1:5 by weight.

3. The product of claim 1, wherein the packed ratio of (a) to (b) ranges from about 20:1 to 2:1 by weight.

4. The product of claim 1, wherein the packed ratio of (a) to (b) ranges from about 20:1 to 4:1 by weight.

* * * * *